US008664469B2

(12) United States Patent
Veith et al.

(10) Patent No.: US 8,664,469 B2
(45) Date of Patent: *Mar. 4, 2014

(54) DISPOSABLE ABSORBENT ARTICLE WITH OVERLAPPING ABSORBENT ASSEMBLY SECURED TO FRONT AND BACK PANELS

(75) Inventors: Jerome Steven Veith, Menasha, WI (US); Paul VanGompel, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/404,586

(22) Filed: Feb. 24, 2012

(65) Prior Publication Data

US 2012/0157956 A1    Jun. 21, 2012

Related U.S. Application Data

(63) Continuation of application No. 12/556,343, filed on Sep. 9, 2009, now Pat. No. 8,147,476, which is a continuation of application No. 10/449,988, filed on May 30, 2003, now Pat. No. 7,604,624.

(51) Int. Cl.
*A61F 13/15* (2006.01)

(52) U.S. Cl.
USPC ........... 604/367; 604/371; 604/378; 604/383; 604/385.22; 604/396; 604/392; 604/387

(58) Field of Classification Search
USPC ............ 604/367, 371, 378, 383, 385.22, 396, 604/392, 386, 387, 389, 394, 385.29; 428/131–140, 315; 442/370; 156/259, 156/258, 227, 204, 238, 160, 229
See application file for complete search history.

(56) References Cited

U.S. PATENT DOCUMENTS

| 1,696,909 | A | 1/1929 | Gillespie |
| 2,166,012 | A | 7/1939 | La Maida |
| 2,544,620 | A | 3/1951 | Steinert |

(Continued)

FOREIGN PATENT DOCUMENTS

| EP | 0 213 642 A2 | 3/1987 |
| EP | 0 323 634 A2 | 7/1989 |

(Continued)

OTHER PUBLICATIONS

American Society for Testing Materials (ASTM) Designation: D2433-93 (Reapproved 2002), "Standard Test Methods for Rubber Thread," pp. 1-6, published Feb. 2003.

(Continued)

*Primary Examiner* — Jacqueline F. Stephens
(74) *Attorney, Agent, or Firm* — Kimberly-Clark Worldwide, Inc.

(57) ABSTRACT

A disposable absorbent article has front and back panels, each having an elastic film layer and each having first and second zones. The first zone of each panel is extensible and retractable and the second zone of each panel is non-extensible and non-retractable. Each of the front and back panels has first and second side edges. An absorbent assembly is secured to the front and back panels. The absorbent assembly has a first end secured to the second zone of the front panel and a second end secured to the second zone of the back panel. A pair of seams join the front and back panels together at the first and second side edges to form a disposable absorbent article having a waist opening and a pair of leg openings.

20 Claims, 5 Drawing Sheets

(56) References Cited

U.S. PATENT DOCUMENTS

| | | |
|---|---|---|
| 2,748,772 A | 6/1956 | Titone et al. |
| 2,749,912 A | 6/1956 | Teitler |
| 3,098,484 A | 7/1963 | Younger |
| 3,237,625 A | 3/1966 | Johnson |
| 3,368,563 A | 2/1968 | Scheier |
| 3,424,162 A | 1/1969 | Parravicini |
| 4,031,568 A | 6/1977 | Huff |
| 4,036,233 A | 7/1977 | Kozak |
| 4,059,973 A | 11/1977 | Gresillon |
| 4,227,531 A | 10/1980 | McLeod |
| 4,300,967 A | 11/1981 | Sigl |
| 4,319,572 A | 3/1982 | Widlund et al. |
| 4,327,448 A | 5/1982 | Lunt |
| 4,355,425 A | 10/1982 | Jones et al. |
| 4,388,075 A | 6/1983 | Mesek et al. |
| 4,437,860 A | 3/1984 | Sigl et al. |
| 4,450,026 A | 5/1984 | Pieniak et al. |
| 4,486,192 A | 12/1984 | Sigl |
| 4,507,163 A | 3/1985 | Menard |
| 4,543,154 A | 9/1985 | Reiter |
| 4,563,185 A | 1/1986 | Reiter |
| 4,606,964 A | 8/1986 | Wideman |
| 4,610,685 A | 9/1986 | Raley |
| 4,615,695 A | 10/1986 | Cooper |
| 4,639,949 A | 2/1987 | Ales et al. |
| 4,663,220 A | 5/1987 | Wisneski et al. |
| 4,681,580 A | 7/1987 | Reising et al. |
| 4,707,398 A | 11/1987 | Boggs |
| 4,710,189 A | 12/1987 | Lash |
| 4,720,415 A | 1/1988 | Vander Wielen et al. |
| 4,724,184 A | 2/1988 | Killian et al. |
| 4,741,949 A | 5/1988 | Morman et al. |
| 4,743,241 A | 5/1988 | Igaue et al. |
| 4,747,846 A | 5/1988 | Boland et al. |
| 4,756,709 A | 7/1988 | Stevens |
| 4,762,521 A | 8/1988 | Roessler et al. |
| 4,770,656 A | 9/1988 | Proxmire et al. |
| 4,789,699 A | 12/1988 | Kieffer et al. |
| 4,808,176 A | 2/1989 | Kielpikowski |
| 4,816,026 A | 3/1989 | Richardson |
| 4,820,572 A | 4/1989 | Killian et al. |
| 4,850,989 A | 7/1989 | Villez |
| 4,863,779 A | 9/1989 | Daponte |
| 4,872,871 A | 10/1989 | Proxmire et al. |
| 4,895,568 A | 1/1990 | Enloe |
| 4,908,247 A | 3/1990 | Baird et al. |
| 4,909,804 A | 3/1990 | Douglas, Sr. |
| 4,923,742 A | 5/1990 | Killian et al. |
| 4,938,754 A | 7/1990 | Mesek |
| 4,940,464 A | 7/1990 | Van Gompel et al. |
| 4,968,312 A | 11/1990 | Khan |
| 4,981,747 A | 1/1991 | Morman |
| 5,004,466 A | 4/1991 | Uda et al. |
| 5,019,066 A | 5/1991 | Freeland et al. |
| 5,163,932 A | 11/1992 | Nomura et al. |
| 5,169,706 A | 12/1992 | Collier, IV et al. |
| 5,204,997 A | 4/1993 | Suzuki et al. |
| 5,226,992 A | 7/1993 | Morman |
| 5,260,126 A | 11/1993 | Collier, IV et al. |
| 5,288,791 A | 2/1994 | Collier, IV et al. |
| 5,336,545 A | 8/1994 | Morman |
| 5,366,793 A | 11/1994 | Fitts, Jr. et al. |
| 5,385,775 A | 1/1995 | Wright |
| 5,486,273 A | 1/1996 | Widlund et al. |
| 5,500,063 A | 3/1996 | Jessup |
| 5,503,908 A | 4/1996 | Faass |
| 5,514,470 A | 5/1996 | Haffner et al. |
| 5,545,158 A | 8/1996 | Jessup |
| 5,554,145 A | 9/1996 | Roe et al. |
| 5,569,232 A | 10/1996 | Roe et al. |
| 5,575,783 A | 11/1996 | Clear et al. |
| 5,599,417 A | 2/1997 | Glaug et al. |
| 5,601,547 A | 2/1997 | Kato et al. |
| 5,607,416 A | 3/1997 | Yamamoto et al. |
| 5,622,581 A | 4/1997 | Ducker et al. |
| 5,624,424 A | 4/1997 | Saisaka et al. |
| 5,643,396 A | 7/1997 | Rajala et al. |
| 5,660,657 A | 8/1997 | Rajala et al. |
| 5,669,996 A | 9/1997 | Jessup |
| 5,683,376 A | 11/1997 | Kato et al. |
| 5,690,627 A | 11/1997 | Clear et al. |
| 5,711,832 A | 1/1998 | Glaug et al. |
| 5,735,839 A | 4/1998 | Kawaguchi et al. |
| 5,745,922 A | 5/1998 | Rajala et al. |
| 5,749,866 A | 5/1998 | Roe et al. |
| 5,772,649 A | 6/1998 | Siudzinski |
| 5,807,368 A | 9/1998 | Helmer |
| 5,827,259 A | 10/1998 | Laux et al. |
| 5,836,930 A | 11/1998 | Lantz et al. |
| 5,846,232 A | 12/1998 | Serbiak et al. |
| 5,855,574 A | 1/1999 | Kling et al. |
| 5,876,391 A | 3/1999 | Roe et al. |
| 5,879,500 A | 3/1999 | Herrin et al. |
| 5,904,673 A | 5/1999 | Roe et al. |
| 5,904,675 A | 5/1999 | Laux et al. |
| 5,906,604 A | 5/1999 | Ronnberg et al. |
| 5,916,206 A | 6/1999 | Otsubo et al. |
| 5,932,497 A | 8/1999 | Morman et al. |
| 5,940,887 A | 8/1999 | Rajala et al. |
| 5,947,948 A | 9/1999 | Roe et al. |
| 5,968,031 A | 10/1999 | Schmitz |
| 5,971,970 A | 10/1999 | Carlbark et al. |
| 6,049,916 A | 4/2000 | Rajala et al. |
| 6,098,203 A | 8/2000 | Rajala et al. |
| 6,129,720 A | 10/2000 | Blenke et al. |
| 6,132,409 A | 10/2000 | Vogt et al. |
| 6,132,410 A | 10/2000 | Van Gompel et al. |
| 6,135,975 A | 10/2000 | Johnstone |
| 6,187,425 B1 | 2/2001 | Bell et al. |
| 6,193,701 B1 | 2/2001 | Van Gompel et al. |
| 6,217,563 B1 | 4/2001 | Van Gompel et al. |
| 6,217,690 B1 | 4/2001 | Rajala et al. |
| 6,240,569 B1 | 6/2001 | Van Gompel et al. |
| 6,248,097 B1 | 6/2001 | Beitz et al. |
| 6,260,211 B1 | 7/2001 | Rajala et al. |
| 6,264,641 B1 | 7/2001 | Van Gompel et al. |
| 6,312,420 B1 | 11/2001 | Sasaki et al. |
| 6,313,372 B1 | 11/2001 | Suzuki |
| 6,322,547 B1 | 11/2001 | Hansson |
| 6,322,552 B1 | 11/2001 | Blenke et al. |
| 6,323,389 B1 | 11/2001 | Thomas et al. |
| 6,325,787 B1 | 12/2001 | Roe et al. |
| 6,336,921 B1 | 1/2002 | Kato et al. |
| 6,336,922 B1 | 1/2002 | VanGompel et al. |
| 6,340,782 B1 | 1/2002 | Kling et al. |
| 6,358,350 B1 | 3/2002 | Glaug et al. |
| 6,361,527 B1 | 3/2002 | Van Gompel et al. |
| 6,364,863 B1 | 4/2002 | Yamamoto et al. |
| 6,375,646 B1 | 4/2002 | Widlund et al. |
| 6,387,471 B1 | 5/2002 | Taylor et al. |
| 6,454,750 B1 | 9/2002 | Vogt et al. |
| 6,464,677 B1 | 10/2002 | Noguchi et al. |
| 6,465,073 B1 | 10/2002 | Morman et al. |
| 6,478,785 B1 | 11/2002 | Ashton et al. |
| 6,482,278 B1 | 11/2002 | McCabe et al. |
| 6,541,679 B2 | 4/2003 | Betrabet et al. |
| 6,551,294 B1 | 4/2003 | Elsberg et al. |
| 6,551,430 B1 | 4/2003 | Glaug et al. |
| 6,570,056 B1 | 5/2003 | Tanzer et al. |
| 6,572,601 B2 | 6/2003 | Suprise et al. |
| 6,595,975 B2 | 7/2003 | Vogt et al. |
| 6,755,808 B2 | 6/2004 | Balogh et al. |
| 7,108,759 B2 | 9/2006 | You et al. |
| 7,264,686 B2 | 9/2007 | Thorson et al. |
| 2002/0002021 A1 | 1/2002 | May et al. |
| 2002/0007148 A1 | 1/2002 | May et al. |
| 2002/0007164 A1 | 1/2002 | Boggs et al. |
| 2002/0009940 A1 | 1/2002 | May et al. |
| 2002/0019616 A1 | 2/2002 | Thomas |
| 2002/0104608 A1 | 8/2002 | Welch et al. |
| 2002/0119722 A1 | 8/2002 | Welch et al. |
| 2002/0128617 A1 | 9/2002 | Roe et al. |
| 2002/0152540 A1 | 10/2002 | Van Gompel et al. |
| 2002/0169432 A1 | 11/2002 | Fell et al. |

(56) References Cited

U.S. PATENT DOCUMENTS

| | | |
|---|---|---|
| 2003/0055389 A1 | 3/2003 | Sanders et al. |
| 2003/0088230 A1 | 5/2003 | Balogh et al. |
| 2003/0124303 A1 | 7/2003 | Price et al. |
| 2003/0125690 A1 | 7/2003 | Hermansson et al. |
| 2003/0135191 A1 | 7/2003 | Price et al. |
| 2003/0135192 A1 | 7/2003 | Guralski et al. |
| 2004/0045924 A1 | 3/2004 | Naritomi et al. |
| 2004/0082933 A1 | 4/2004 | Karami |
| 2004/0116887 A1 | 6/2004 | Thorson et al. |
| 2004/0122400 A1 | 6/2004 | Hancock Cooke et al. |
| 2004/0122404 A1 | 6/2004 | Meyer et al. |
| 2004/0122405 A1 | 6/2004 | Van Gompel et al. |
| 2004/0122411 A1 | 6/2004 | Hancock Cooke |
| 2004/0210205 A1 | 10/2004 | VanGompel et al. |
| 2004/0243085 A1 | 12/2004 | Veith et al. |
| 2004/0243086 A1 | 12/2004 | VanGompel et al. |
| 2005/0004549 A1 | 1/2005 | Maas et al. |
| 2005/0020992 A1 | 1/2005 | Van Gompel et al. |
| 2005/0107763 A1 | 5/2005 | Matsuda et al. |
| 2005/0131365 A1 | 6/2005 | Sakaguchi |

FOREIGN PATENT DOCUMENTS

| | | |
|---|---|---|
| EP | 0 357 298 A2 | 3/1990 |
| EP | 0 404 648 A1 | 12/1990 |
| EP | 0 456 885 A1 | 11/1991 |
| EP | 0 460 467 A1 | 12/1991 |
| EP | 0 526 868 A2 | 2/1993 |
| EP | 0 528 282 A2 | 2/1993 |
| EP | 0 650 714 A1 | 5/1995 |
| EP | 0 597 331 B1 | 11/1997 |
| EP | 0 630 221 B2 | 11/2000 |
| EP | 1 072 243 A2 | 1/2001 |
| EP | 1 157 681 A2 | 11/2001 |
| EP | 1 184 017 A1 | 3/2002 |
| EP | 1 240 881 A2 | 9/2002 |
| EP | 1 247 505 A2 | 10/2002 |
| EP | 1 247 506 A2 | 10/2002 |
| EP | 1 249 214 A2 | 10/2002 |
| EP | 1 374 814 A1 | 1/2004 |
| EP | 1 393 701 A2 | 3/2004 |
| EP | 1 428 487 A1 | 6/2004 |
| GB | 2 253 131 A | 9/1992 |
| GB | 2 297 474 A | 8/1996 |
| JP | 03-176053 A | 7/1991 |
| JP | 03-195555 A | 8/1991 |
| JP | 03-205053 A | 9/1991 |
| JP | 04-089050 A | 3/1992 |
| JP | 04-354948 A | 12/1992 |
| JP | 11-318978 A | 11/1999 |
| JP | 2000-279447 A | 10/2000 |
| JP | 2003-339771 A | 12/2003 |
| JP | 2004-089403 A | 3/2004 |
| WO | WO 95/02382 A1 | 1/1995 |
| WO | WO 95/02383 A1 | 1/1995 |
| WO | WO 96/08224 A2 | 3/1996 |
| WO | WO 96/11236 A1 | 4/1996 |
| WO | WO 96/23466 A1 | 8/1996 |
| WO | WO 96/32083 A1 | 10/1996 |
| WO | WO 97/23180 A1 | 7/1997 |
| WO | WO 97/43994 A1 | 11/1997 |
| WO | WO 98/29251 A1 | 7/1998 |
| WO | WO 98/53785 A1 | 12/1998 |
| WO | WO 99/56688 A1 | 11/1999 |
| WO | WO 99/60967 A1 | 12/1999 |
| WO | WO 99/60968 A1 | 12/1999 |
| WO | WO 99/60971 A1 | 12/1999 |
| WO | WO 99/60972 A1 | 12/1999 |
| WO | WO 99/60974 A1 | 12/1999 |
| WO | WO 00/02511 A1 | 1/2000 |
| WO | WO 00/37005 A2 | 6/2000 |
| WO | WO 00/39201 A2 | 7/2000 |
| WO | WO 01/87212 A1 | 11/2001 |
| WO | WO 02/069871 A1 | 9/2002 |
| WO | WO 03/002052 A1 | 1/2003 |
| WO | WO 03/017903 A1 | 3/2003 |
| WO | WO 03/028604 A1 | 4/2003 |
| WO | WO 2004/054490 A1 | 7/2004 |

OTHER PUBLICATIONS

American Society for Testing Materials (ASTM) Designation: D5459-95, (Reapproved 2001) "Standard Test Method for Machine Direction Elastic Recovery and Permanent Deformation and Stress Retention of Stretch Wrap Film," pp. 731-733, published Sep. 1995.

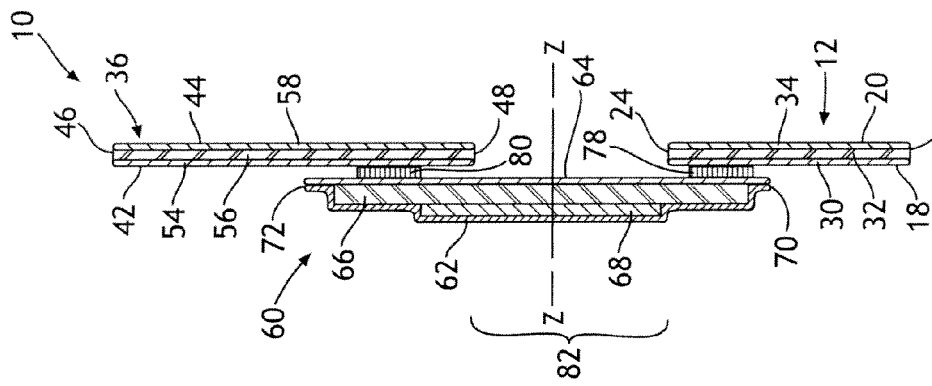
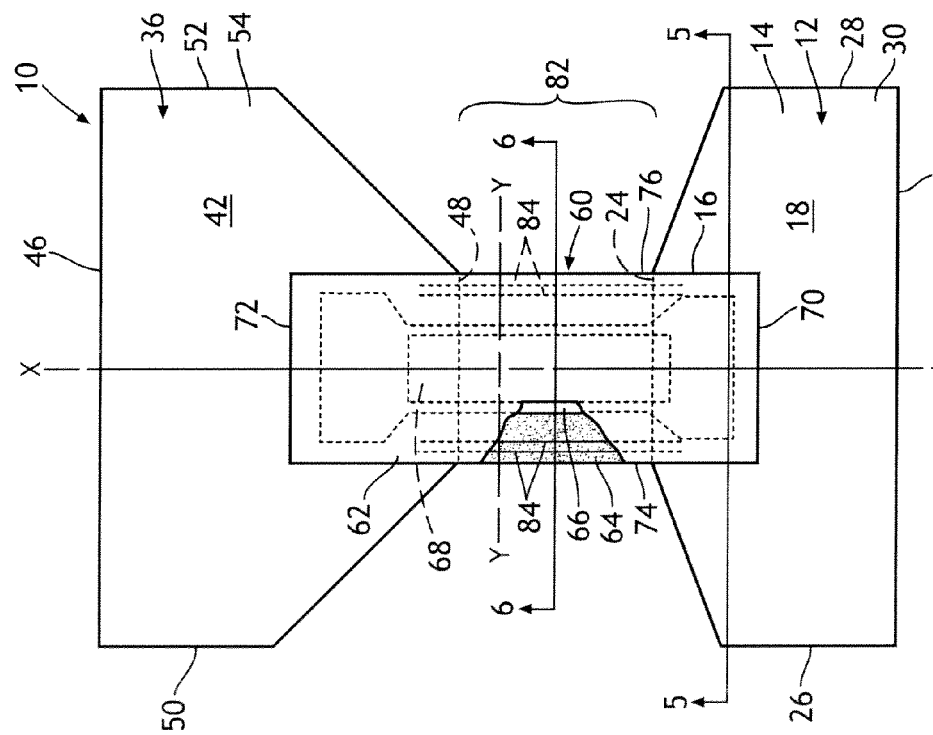

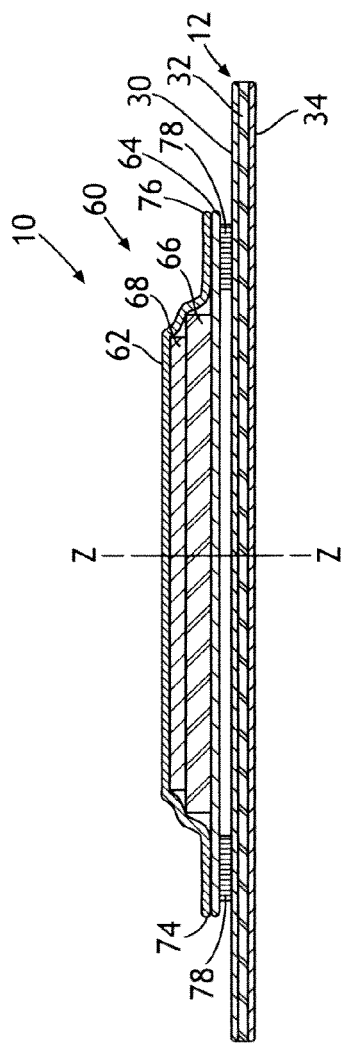
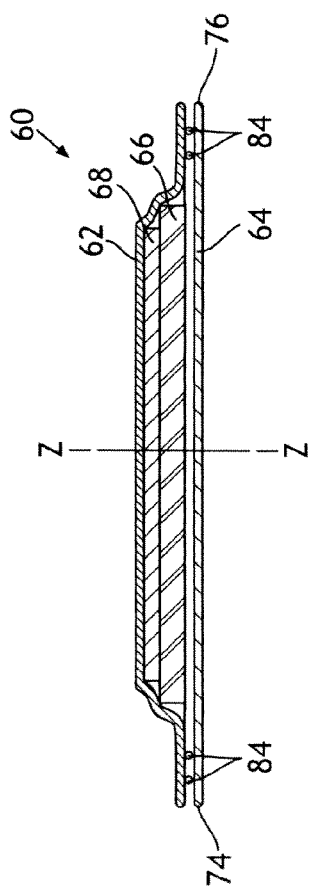

```
┌─────────────────────────────────────────────────────────────────┐
│ FORMING A FRONT PANEL HAVING AN EXTENSIBLE AND RETRACTABLE      │
│ FIRST ZONE AND A NON-EXTENSIBLE AND NON-RETRACTABLE SECOND      │
│ ZONE                                                            │
└─────────────────────────────────────────────────────────────────┘
                                │
┌─────────────────────────────────────────────────────────────────┐
│ FORMING A BACK PANEL HAVING AN EXTENSIBLE AND RETRACTABLE       │
│ FIRST ZONE AND A NON-EXTENSIBLE AND NON-RETRACTABLE SECOND      │
│ ZONE                                                            │
└─────────────────────────────────────────────────────────────────┘
                                │
┌─────────────────────────────────────────────────────────────────┐
│ FORMING AN ABSORBANT ASSEMBLY HAVING A LIQUID PERVIOUS          │
│ BODYSIDE LINER, A LIQUID-IMPERVIOUS OUTER COVER, AND AN         │
│ ABSORBANT POSITIONED THEREBETWEEN                               │
└─────────────────────────────────────────────────────────────────┘
                                │
┌─────────────────────────────────────────────────────────────────┐
│ SECURING SAID ABSORBANT ASSEMBLY TO SAID SECOND ZONES OF        │
│ BOTH SAID FRONT AND BACK PANELS                                 │
└─────────────────────────────────────────────────────────────────┘
                                │
┌─────────────────────────────────────────────────────────────────┐
│ FOLDING SAID ABSORBANT ASSEMBLY SO THAT SAID FRONT PANEL IS     │
│ POSITIONED OVER SAID BACK PANEL                                 │
└─────────────────────────────────────────────────────────────────┘
                                │
┌─────────────────────────────────────────────────────────────────┐
│ JOINING SAID FRONT PANEL TO SAID BACK PANEL BY A PAIR OF SEAMS  │
│ TO FORM A DISPOSABLE ABSORBANT ARTICLE HAVING A WAIST           │
│ OPENING AND A PAIR OF LEG OPENINGS                              │
└─────────────────────────────────────────────────────────────────┘
```

FIG. 7

DISPOSABLE ABSORBENT ARTICLE WITH OVERLAPPING ABSORBENT ASSEMBLY SECURED TO FRONT AND BACK PANELS

This application is a continuation of application Ser. No. 12/556,343 filed on Sep. 9, 2009 now U.S. Pat. No. 8,147,476 and application Ser. No. 10/449,988 filed on May 30, 2003, now U.S. Pat. No. 7,604,624. The entirety of application Ser. No. 12/556,343 and U.S. Pat. No. 7,604,624 are hereby incorporated by reference.

BACKGROUND OF THE INVENTION

A disposable absorbent article is designed for absorbing human exudate. The disposable absorbent article is similar in appearance, size and shape to a regular cloth underwear except that it is not designed to be laundered and reused two or more times. A disposable absorbent article is intended to be worn by persons, including infants, toddlers, or adults, and is designed for single or temporary use. The disposable absorbent article is meant to be disposed of after being used once. The disposable absorbent article is designed to be pulled up around the user's torso without having to first open the garment in order to place it on a person's body. The stretchability of the material used to construct the disposable absorbent article permits the garment to snugly conform to the anatomy of the user's torso. The disposable absorbent article can be manufactured to be an infant diaper, a child training pant, an adult incontinence garment, a feminine menstrual pant, etc.

Some disposable absorbent articles manufactured today resemble regular cloth underwear in that they have a waist opening and a pair of leg openings. Such disposable absorbent articles can be pulled up around the torso of a user in a similar fashion as regular cloth underwear. It has been found that a disposable absorbent article is generally more discreet when the front and back elastic panels snugly conform to the wearer's anatomy. It has also been found that a more comfortable article is obtained when the absorbent assembly does not extend and retract to match the movement of the front and back elastic panels.

Now a disposable absorbent article for absorbing human exudate has been invented that allows the front and back elastic panels to extend and retract without causing the absorbent assembly to move in a similar fashion thereby providing a better fit to the user's body.

SUMMARY OF THE INVENTION

Briefly, this invention relates to a disposable absorbent article for absorbing human exudate and a method of forming the article. The disposable absorbent article includes a front panel and a back panel with each having a first zone and a second zone. The first zone is extensible and retractable and the second zone is non-extensible and non-retractable. Each of the front and back panels also has an inner surface and first and second side edges. The second zone of each panel is spaced inward from the first and second side edges. An absorbent assembly bridges across and is secured to the front and back panels. The absorbent assembly includes a liquid pervious bodyside liner, a liquid-impervious outer cover and an absorbent positioned therebetween. The absorbent assembly has a first end and a second end. The first end is secured to the second zone of the front panel and the second end is secured to the second zone of the back panel. The absorbent assembly is capable of being folded to enable the first and second side edges of the front panel to align with the first and second side edges of the back panel, respectively. A pair of seams join the front and back panels together at the first and second side edges to form a disposable absorbent article having a waist opening and a pair of leg openings.

BRIEF DESCRIPTION OF THE DRAWINGS

FIG. 3 is a plane view of a disposable absorbent article showing an absorbent assembly secured to the inner surfaces of the front and back panels and showing a partial cut away view of the construction of the absorbent assembly.

FIG. 4 is a side view of the disposable absorbent article shown in FIG. 3.

FIG. 5 is a cross-sectional view of the disposable absorbent article shown in FIG. 3 taken along line 5-5.

FIG. 6 is a cross-sectional view of the disposable absorbent article shown in FIG. 3 taken along line 6-6.

FIG. 7 is a flow diagram of a method used to manufacture the disposable absorbent article of this invention.

DETAILED DESCRIPTION

Figure 1:
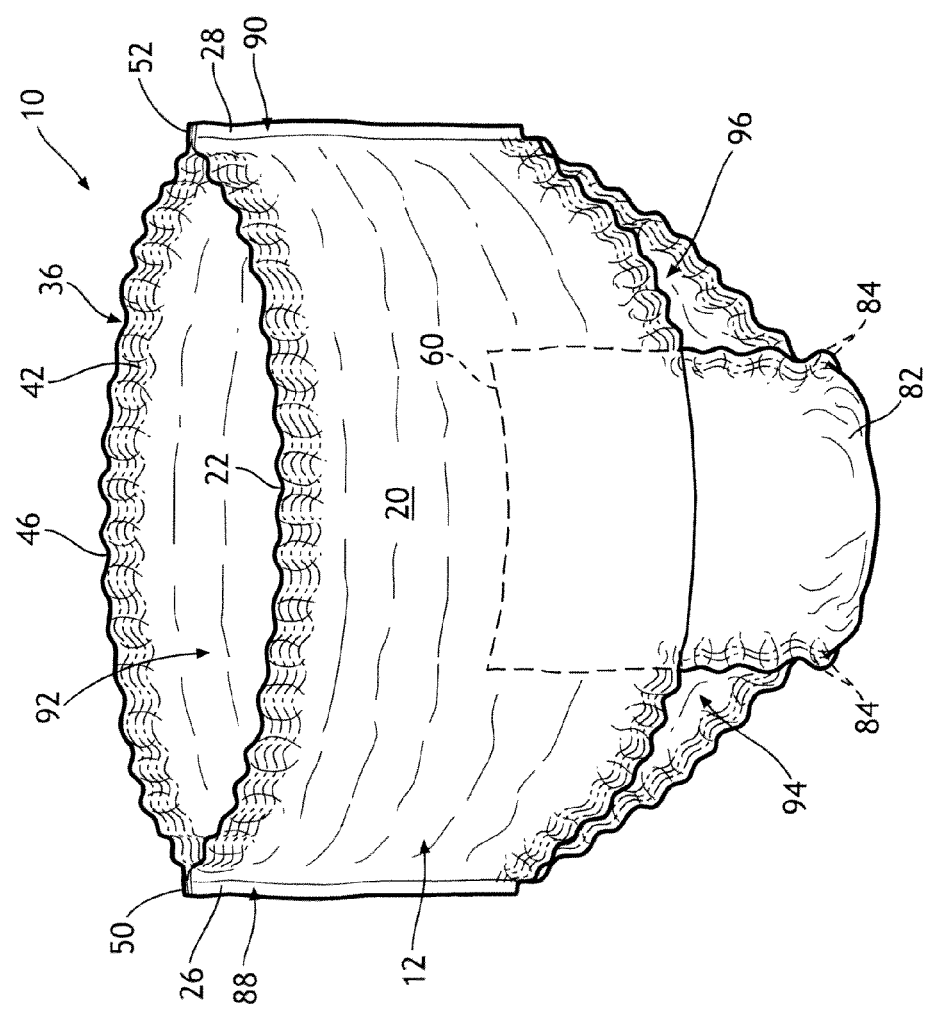
FIG. 1 is a perspective view of a disposable absorbent article.

Referring to FIG. 1, a disposable absorbent article 10 is depicted. The disposable absorbent article 10 is intended to be worn by persons, including infants, toddlers, or adults, and is designed for a single or temporary use. The disposable absorbent article 10 is meant to be disposed of after being used once instead of being laundered or dry cleaned for re-use. The term "disposable absorbent article" is herein defined to mean an absorbent article that is inexpensive and can be discarded by the consumer once it becomes soiled or otherwise unusable after a single use or after a few uses. In the context of disposable personal care absorbent articles, such articles are normally disposed of after they are soiled and are not meant to be laundered or treated for re-use and are distinguishable from limited use articles that can be used several times before being discarded, such as disposable razors and cigarette lighters. The disposable absorbent article 10 is designed to be pulled up around the user's torso without having to first open the article 10 in order to place it on a person's body. In FIG. 1, the disposable absorbent article 10 is shown as it would appear just prior to being pulled up around a user's torso.

Figure 2:
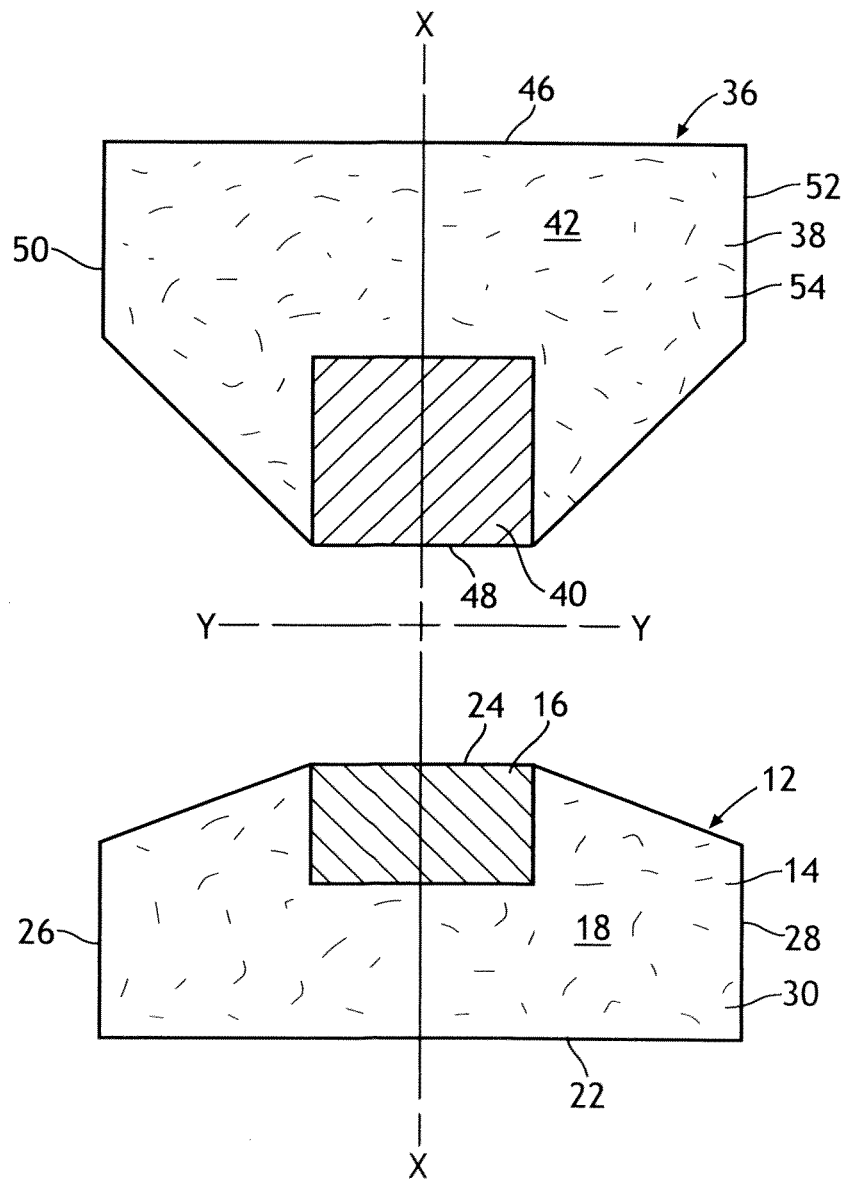
FIG. 2 is a top view of the spaced apart front and back panels showing the first and second zones.

Referring to FIGS. 2-4, the disposable absorbent article 10 has a longitudinal central axis X-X, a transverse central axis Y-Y, and a vertical central axis Z—Z. The disposable absorbent article 10 includes a front panel 12 having a first zone 14 and a second zone 16. The first zone 14 is extensible and retractable in at least one direction. Desirably, the first zone 14 is extensible and retractable in two or more directions. When the first zone 14 is extensible and retractable in only one direction, that direction should be approximately parallel to the transverse central axis Y-Y of the disposable absorbent article 10. The second zone 16 is non-extensible and non-retractable. The second zone 16 can be of any geometrical configuration but a rectangular or square configuration works well. The second zone 16 has a surface area that is smaller than the surface area of the first zone 14. Desirably, the second zone 16 has a surface area that is less than about 25% of the surface area of the first zone 14. More desirably, the second zone 16 has a surface area that is less than about 20% of the surface area of the first zone 14. Most desirably, the second zone 16 has a surface area that is less than about 15% of the surface area of the first zone 14.

Still referring to FIGS. 2-4, the front panel 12 also includes an inner surface 18 and an outer surface 20. The inner surface 18 is in direct contact with the user's skin and is sometimes referred to as the bodyside surface. The outer surface 20 is situated opposite to the inner surface 18 and is spaced away from the skin of the user. The outer surface 20 is sometimes referred to as the garment facing surface since it can be in direct contact with the inner surfaces of the user's outer clothing.

Referring to FIG. 2, the front panel 12 further includes a first end 22, a second end 24, a first side edge 26 and a second side edge 28. The overall size and shape of the front panel 12 can vary to suit the size and anatomy of the actual user. For example, the front panel 12 of an infant diaper will be smaller than the front panel 12 of an adult incontinence garment. The first and second zones, 14 and 16 respectively, can be integrally formed from a single material or they can be formed from separate and distinct materials. The second zone 16 is spaced inward from the first and second side edges 26 and 28. The second zone 16 is also shown having an edge that is coterminuous with the second end 24 of the front panel 12. The second zone 16 is located adjacent to or in an abutting relationship to the first zone 14. However, the second zone 16 should not overlay or be covered by any portion of the first zone 14. Desirably, the second zone 16 is surrounded on three sides by the first zone 14, as is shown in FIG. 2.

The front panel 12 can be formed from a material that is extensible and retractable in at least one direction. By "extensible" it is meant a material that is capable of being stretched, extended or elongated when a force, such as pulling, is applied to it. By "retractable" it is meant a material that is capable of quickly recovering, retracting or returning to substantially its pre-stretched, pre-extended dimension once the force used to extend the material has been removed. Because of hysteresis, a material might not be able to fully recover or return to its original pre-stretched length. Some materials might be extensible but are not retractable. For example, many conventional textile and non-woven materials, that lack an elastic component, are extensible but lack retractability to return rapidly to substantially their pre-stretched dimension. Such materials, including but not limited to, a cotton knit T-shirt material or blends of cotton and non-elastic synthetic fibers can be extended but are not considered retractable for the purposes of this invention unless some elasticizing material, agent or treatment is added.

The front panel 12 can be formed from an elastomeric material. An elastomeric material can be a single elastic sheet or layer, an elastic film, an elastic net-like material, a plurality of elastic strands arranged to form an elastic layer, an elastic laminate, etc. When a plurality of elastic strands is utilized, they can be positioned on at least one layer of woven or non-woven material. When an elastic laminate is used, it can consist of two or more layers bonded together by heat, pressure, heat and pressure, adhesives, ultrasonics, or a combination of any of the above. Other means of securing one or more layers together to form a laminate structure are known to those skilled in the art. In a laminate, only one of the layers needs to be an elastomeric layer.

Referring now to FIGS. 3 and 4, the front panel 12 is shown being formed as a three-layer laminate structure. The front panel 12 includes a first layer 30, a second or middle layer 32, and a third layer 34. The first and third layers, 30 and 34 respectively, are the outer layers and can be formed from the same material or from different materials. The first and third layers, 30 and 34 respectively, can be constructed from natural or synthetic fibers and can be a woven or non-woven material. The second or middle layer 32 has the elastic properties and is sandwiched between the first and third layers, 30 and 34 respectively. It should be noted that one or both of the outer layers 30 or 34 can be made from an elastic material, if desired.

The extensible and retractable properties of the first zone 14 of the front panel 12 can be in one direction but desirably are in two or more directions. More desirably, the extensible and retractable properties of the first zone 14 are in a direction approximately parallel to the transverse central axis Y-Y. The transverse direction extends laterally across the torso of the user of the disposable absorbent article 10 and extends from one hip bone to the other hip bone. Even more desirably, the extensible and retractable properties of the first zone 14 are in at least two directions, one direction being approximately parallel to the longitudinal central axis X-X and the other direction being approximately parallel to the transverse central axis Y-Y. Most desirably, the extensible and retractable properties of the first zone 14 are in multiple directions, or stated another way, in three or more directions extending over an arc of 360 degrees. The ability of the first zone 14 to extend and retract will provide the requisite force needed during use of the disposable absorbent article 10 to ensure that it snugly conforms to the anatomy of the wearer's torso.

The front panel 12 can be constructed from various materials. One suitable material is a stretch bonded laminate (SBL) where the elastic core or middle layer 32 is elongated before the two outer nonwoven layers 30 and 34 are attached. Exemplary SBL materials are described in U.S. Pat. No. 4,720,415 which is hereby incorporated by reference and made a part hereof. Another suitable material for the front panel 12 is a necked bonded laminate (NBL). The NBL material is also a three-layer laminate but the elastic core or middle layer 32 is not pre-stretched prior to being attached to the two outer nonwoven layers 30 and 34. Instead, the outer layers 30 and 34 are necked stretched before the elastic core or middle layer 32 is attached to them. Exemplary NBL materials are described in U.S. Pat. No. 5,336,545 which is hereby incorporated by reference and made a part hereof. Other examples of elastomeric materials that can be used for the front panel 12 include a continuous filament stretch bonded laminate (CFSBL), a vertical filament laminate (VFL), a necked stretch bonded laminate (NSBL) and a necked thermal laminate (NTL). Combinations of the above materials can also be used. Exemplary CFSBL materials are described in U.S. Pat. No. 5,385,775 which is hereby incorporated by reference and made a part hereof.

Furthermore, the front panel 12 can be constructed from an elastic film that is capable of being stretched in at least one direction. Desirably, the front panel 12 can be stretched in both the machine direction (approximately parallel to the longitudinal central axis X-X) and the cross-direction (approximately parallel to the transverse central axis Y-Y). The front panel 12 can also be formed from an elastic nonwoven that has a machine direction stretch and/or a cross-direction stretch.

Still further, the front panel 12 can be formed from two outer layers 30 and 34 with a plurality of elastic strands sandwiched therebetween. The elastic strands can be formed from Lycra®. Lycra® is a registered trademark of E. I. Du Pont De Nemours & Co., having an office at 1007 Market Street, Wilmington, Del. 19898. The elastic strands can be aligned approximately parallel to one another or be angled or skewed relative to one another. The elastic strands can also be uniformly or randomly spaced apart from one another. The elastic strands can vary in shape, size, configuration, and/or length. The diameter and/or cross-sectional configuration of the elastic strands, the decitex (weight in grams per 10,000 meters of a strand) of the elastic strands, and the tension imparted into the elastic strands can all be varied to suit one's particular product needs. The elastic strands can have a round, semi-circular, square, rectangular, oval or some other geometrical configuration. The elastic strands can overlap, intersect or crisscross at least one other elastic strand. The various ways of positioning, orienting, and adhering the elastic strands to the two outer layers 30 and 34 are well known to those skilled in the art.

It should be noted that the front panel 12 can also be constructed from a material that is substantially air permeable, if desired. Alternatively, the front panel 12 can be constructed from a material that is substantially air impermeable.

The front panel 12 can be formed from a single integral elastomeric material that exhibits both extensible and retractable characteristics. The material can then be treated, fused, deadened, chopped, conditioned or somehow altered so as to form the second zone 16. The elastic properties of the material can be deadened before, during or after the material is stretched. Hammering the material between two hardened surfaces can cause the material to lose its extensible and retractable properties in a given area. The material can also be treated with heat, pressure, heat and pressure, ultrasonics, chemicals, by mechanical means, or a combination of the above to remove its ability to elongate and retract. In this fashion, the second zone 16 can be formed. Alternatively, the second zone 16 can be a separated material that does not possess any extensible and retractable properties. In this case, the second zone 16 is secured to the first zone 14 in order to construct the front panel 12.

Referring again to FIG. 2, one can see that the first zone 14 of the front panel 12 encloses three sides of the second zone 16. Likewise, the first zone 38 of the back panel 36 encloses three sides of the second zone 40. This construction ensures that the second zones 16 and 40 are situated adjacent to an end, 24 or 48 respectively, of the front and back panels, 12 and 36 respectively.

Referring again to FIGS. 2-4, the disposable absorbent article 10 also includes a back panel 36 which is spaced apart, discontinuous and distinct from the front panel 12. The back panel 36 has a first zone 38 and a second zone 40. The first zone 38 is extensible and retractable in at least one direction. Desirably, the first zone 38 is extensible and retractable in two or more directions. When the first zone 38 is extensible and retractable in only one direction, that direction should be approximately parallel to the transverse central axis Y-Y of the disposable absorbent article 10. The second zone 40 is non-extensible and non-retractable. The second zone 40 can be of any geometrical configuration but a rectangular or square configuration works well. The second zone 40 has a surface area that is smaller than the surface area of the first zone 38. Desirably, the second zone 40 has a surface area that is less than about 30% of the surface area of the first zone 38. More desirably, the second zone 40 has a surface area that is less than about 25% of the surface area of the first zone 38. Most desirably, the second zone 40 has a surface area that is less than about 20% of the surface area of the first zone 38.

It should be noted that the second zone 40 of the back panel 36 has a larger surface area than the second zone 16 of the front panel 12. One reason for this is that the front panel 12 usually has a smaller overall surface area than the back panel 36. The back panel 36 is typically larger in size for it has to cover the buttocks of the user.

Still referring to FIGS. 2-4, the back panel 36 also includes an inner surface 42 and an outer surface 44. The inner surface 42 is in direct contact with the user's skin and is sometimes referred to as the bodyside surface. The outer surface 44 is situated opposite to the inner surface 42 and is spaced away from the skin of the user. The outer surface 44 is sometimes referred to as the garment facing surface since it can be in direct contact with the inner surfaces of the user's outer clothing.

The back panel 36 further includes a first end 46, a second end 48, a first side edge 50 and a second side edge 52. The overall size and shape of the back panel 36 can vary to suit the size and anatomy of the actual user. For example, the back panel 36 for an infant diaper will be smaller than the back panel 36 for an adult incontinence garment. The first and second zones, 38 and 40 respectively, of the back panel 36 can be integrally formed from a single material or they can be formed from separate and distinct material. The second zone 40 is spaced inward from the first and second side edges 50 and 52. The second zone 40 is also shown having an edge that is coterminuous with the second end 48 of the back panel 36. The second zone 40 is located adjacent to or in an abutting relationship to the first zone 38. However, the second zone 40 should not overlay or be covered by any portion of the first zone 38. Desirably, the second zone 40 is surrounded on three sides by the first zone 38, as is shown in FIG. 2.

The back panel 36 can be formed from the same material or from a different material as the front panel 12. The back panel 36 is extensible and retractable in at least one direction. The definitions for "extensible and retractable" are as defined above with reference to the front panel 12. The back panel 36 can be formed from an elastomeric material. An elastomeric material can be a single elastic sheet or layer, an elastic film, an elastic net-like material, a plurality of elastic strands arranged to form an elastic layer, an elastic laminate, etc. When a plurality of elastic strands is utilized, they can be positioned on at least one layer of woven or non-woven material. When an elastic laminate is used, it can consist of two or more layers bonded together by heat, pressure, heat and pressure, adhesives, ultrasonics, or a combination of any of the above. Other means of securing one or more layers together to form a laminate structure are known to those skilled in the art. In a laminate, only one of the layers needs to be an elastomeric layer.

Referring again to FIGS. 3 and 4, the back panel 36 is shown being formed as a three-layer laminate structure. The back panel 36 includes a first layer 54, a second or middle layer 56, and a third layer 58. The first and third layers, 54 and 58 respectively, are the outer layers and can be formed from the same material or from different materials. The first and third layers, 54 and 58 respectively, can be constructed from natural or synthetic fibers and can be a woven or non-woven material. The second or middle layer 56 has the elastic properties and is sandwiched between the first and third layers, 54 and 58 respectively. It should be noted that one or both of the outer layers 54 or 58 can be made from an elastic material, if desired.

The extensible and retractable properties of the first zone 38 of the back panel 36 can be in one direction but desirably are in two or more directions. More desirably, the extensible and retractable properties of the first zone 38 are in a direction approximately parallel to the transverse central axis Y-Y. The transverse direction extends laterally across the torso of the user of the disposable absorbent article 10 and extends from one hip bone to the other hip bone. Even more desirably, the extensible and retractable properties of the first zone 38 are in at least two directions, one direction being approximately parallel to the longitudinal central axis X-X and the other direction being approximately parallel to the transverse central axis Y-Y. Most desirably, the extensible and retractable properties of the first zone 38 are in multiple directions, or stated another way, in three or more directions extending over an arc of 360 degrees. The ability of the first zone 38 to extend and retract will provide the requisite force needed during use of the disposable absorbent article 10 to ensure that it snugly conforms to the anatomy of the wearer's torso.

The back panel 36 can be constructed from various materials. One suitable material is a stretch bonded laminate (SBL) where the elastic core or middle layer 56 is elongated before the two outer nonwoven layers 54 and 58 are attached. Another suitable material for the back panel 36 is a necked bonded laminate (NBL). The NBL material is also a three-layer laminate but the elastic core or middle layer 56 is not pre-stretched prior to being attached to the two outer nonwoven layers 54 and 58. Instead, the outer layers 54 and 58 are necked stretched before the elastic core or middle layer 56 is attached to them. Other examples of such elastomeric materials that can be used for the back panel 36 include a continuous filament stretch bonded laminate (CFSBL), a vertical filament laminate (VFL), a necked stretch bonded laminate (NSBL) or a necked thermal laminate (NTL). Combinations of the above materials can also be used.

Furthermore, the back panel 36 can be constructed from an elastic film that is capable of being stretched in at least one direction and, desirably, in both the machine direction (approximately parallel to the longitudinal central axis X-X) and the cross-direction (approximately parallel to the transverse central axis Y-Y). The back panel 36 can also be formed from an elastic nonwoven that has a machine direction stretch and/or a cross-direction stretch.

Still further, the back panel 36 can be formed from two outer layers 54 and 58 with a plurality of elastic strands sandwiched therebetween. The elastic strands can be formed from Lycra®. Lycra® is a registered trademark of E. I. Du Pont De Nemours & Co., having an office at 1007 Market Street, Wilmington, Del. 19898. The elastic strands can be aligned approximately parallel to one another or be angled or skewed relative to one another. The elastic strands can also be uniformly or randomly spaced apart from one another. The elastic strands can vary in shape, size, configuration, and/or length. The diameter and/or cross-sectional configuration of the elastic strands, the decitex (weight in grams per 10,000 meters of a strand) of the elastic strands, and the tension imparted into the elastic strands can all be varied to suit one's particular product needs. The elastic strands can have a round, semi-circular, square, rectangular, oval or some other geometrical configuration. The elastic strands can overlap, intersect or crisscross at least one other elastic strand. The various ways of positioning, orienting, and adhering the elastic strands to the two outer layers 54 and 58 are well known to those skilled in the art.

It should be noted that the back panel 36 can also be constructed from a material that is substantially air permeable, if desired. Alternatively, the back panel 36 can be constructed from a material that is substantially air impermeable.

The back panel 36 can be formed from a single integral elastomeric material that exhibits both extensible and retractable characteristics. The material can then be treated, fused, deadened, chopped, conditioned or somehow altered so as to form the second zone 40. Hammering the material between two hardened surfaces can also cause the material to lose its extensible and retractable properties in a given area. The material can also be treated with heat, pressure, heat and pressure, ultrasonics, chemicals, by mechanical means, or a combination of the above to remove its ability to elongate and/or retract. In this fashion, the second zone 40 can be formed. Alternatively, the second zone 40 can be a separated material that does not possess any extensible and retractable properties. In this case, the second zone 40 is secured to the first zone 38 in order to construct the back panel 36.

Referring again to FIGS. 1 and 3-5, the disposable absorbent article 10 also includes an absorbent assembly 60. The absorbent assembly 60 includes a liquid pervious bodyside liner 62, a liquid-impervious outer cover 64, and an absorbent 66 positioned therebetween. A surge layer 68 can be optionally used which is located between the bodyside liner 62 and the absorbent 66. The surge layer 68 can function to rapidly acquire and temporarily retain body fluid, such as urine, before it can be absorbed into the absorbent 66. Desirably, the surge layer 68 is also capable of wicking the body fluid lengthwise and/or widthwise across its surface, as well as directing the body fluid downward in a z-direction (approximately parallel to the vertical axis Z—Z) toward the absorbent 66.

The absorbent assembly 60 has a first end 70, a second end 72, a first side edge 74 and a second side edge 76. Desirably, the absorbent assembly 60 is secured to the inner surface 18 of the front panel 12 approximate the first end 70 by an attachment 78 and is secured to the inner surface 42 of the back panel 36 approximate the second end 72 by an attachment 80. Alternatively, the absorbent assembly 60 could be secured to outer surface 20 of the front panel 12 approximate the first end 70 by the attachment 78 and could be secured to the outer surface 44 of the back panel 36 approximate the second end 72 by the attachment 80. The absorbent assembly 60 is secured to the front and back panels, 12 and 36 respectively, either before or after each panel 12 and 36 has been stretched a predetermined amount. By attaching the absorbent assembly 60 to the front and back panels, 12 and 36 respectively, the absorbent assembly 60 is capable of moving downward away from the user's torso while the front and back panels, 12 and 36 respectively, maintain their snug position against the user's torso. This unique ability for the absorbent assembly 60 to move outward and downward away from the user's torso without undue restrictions from the front and back panels, 12 and 36 respectively, produces a useful undergarment. The absorbent assembly 60 is capable of taking in and retaining additional body fluid as it moves out away from the user's body.

The attachments 78 and 80 can be by various means and can include permanent attachments as well as removable or releasable attachments. Desirably, the attachments 78 and 80 are permanent attachments where they are not designed to be removed without destroying the bond. The attachments 78 and 80 can be formed by using glue, adhesive, ultrasonic bonds, heat bonds, pressure bonds, heat and pressure bonds, a combination of any of the aforementioned, etc. The attachments 78 and 80 can also include a mechanical fastener, such as by sewing with thread, using buttons and button holes, using snaps, by employing hook and loop fasteners, etc. A hook and loop fastener is generally considered a releasable attachment. One type of hook and loop fastener is Velcro® wherein a hook material is releasably engaged into a loop material. Velcro® is a registered trademark of Velcro USA, Inc. having an office at 406 Brown Avenue, Manchester, N.H. 03103.

The attachments 78 and 80 can be formed along a continuous line or over a surface area having a predetermined length and width. Alternatively, the attachments 78 and 80 can consist of intermittent point bonds that are spaced apart from one another. For example, the intermittent point bonds can be formed by using a hot or cold melt adhesive or by forming ultrasonic bonds. Various bond formations can be used which are known to those skilled in the art. Desirably, the attachments 78 and 80 are formed using intermittent bonds.

Referring again to FIGS. 3 and 4, one will notice that the absorbent assembly 60 is positioned to overlay the second zones 16 and 40 of the front and back panels, 12 and 36 respectively. Each of the second zones 16 and 40 can have the same width dimension or a width of a different dimension. Desirably, each of the second zones 16 and 40 has a width of the same dimension. The width of the absorbent assembly 60 can be greater than, equal to or less than the width of either of the second zones 16 and 40. However, the absorbent assembly 60 is secured only to the second zones 16 and 40 so as not to extend and retract with the movement of the first zones 14 and 38 of the front and back panels, 12 and 36 respectively. This method of attachment will assure that the absorbent assembly 60 remains relatively stationary while the front and back panels, 12 and 36 respectively, are capable of extending and retracting in correspondence to movement of the user's torso. In FIGS. 3 and 4, one will also notice that the absorbent assembly 60 is positioned such that a greater portion of it is located over the back panel 36 than over the front panel 12. This placement of the absorbent assembly 60 over a greater portion of the back panel 36 provides a better functioning disposable absorbent article 10, especially one that is designed to absorb both body fluid from the penis or vagina, as well as solid and semi-solid excrement from the anus. In addition, the front panel 12 is usually smaller in size than the back panel 36. This size difference also influences the placement of the absorbent assembly 60 over a greater portion of the back panel 36. The result is that the first end 70 of the absorbent assembly 60 is secured to the front panel 12 at a location that is closer to the second end 24 of the front panel 12 than it is to the first end 22. Likewise, the second end 72 of the absorbent assembly 60 is secured to the back panel 36 at a location that is closer to the second end 48 of the back panel 36 than to the first end 46.

Referring now to FIGS. 3-6, one will notice that when the absorbent assembly 60 is secured to the front and back panels, 12 and 36 respectively, a crotch region 82 is formed. The crotch region 82 separates the front panel 12 from the back panel 36 and is designed to cover the perineum area of the wearer. The crotch region 82 can cover a distance of a few inches in an infant diaper to several inches in an adult incontinence garment. For example, a crotch region 82 in an infant diaper may range from about 2 inches (about 5 centimeters (cm)) to about 10 inches (about 25 cm); while in an adult incontinence garment, the crotch region 82 may range from about 6 inches (about 15 cm) to about 20 inches (about 51 cm).

The absorbent assembly 60 can be stretchable or non-stretchable in relation to the front and back panels, 12 and 36 respectively. Desirably, the absorbent assembly 60 is non-stretchable in relation to the front and back panels, 12 and 36 respectively. By having the absorbent assembly 60 be non-stretchable in relation to the front and back panels, 12 and 36 respectively, it is meant that the absorbent assembly 60 will not stretch appreciably in the longitudinal or transverse directions. For example, the absorbent assembly 60 will have less than about 50% of the stretch of the front and/or back panels, 12 and/or 36 respectively. Desirably, the absorbent assembly 60 will have less than about 25% of the stretch of the front and/or back panels, 12 and/or 36 respectively. More desirably, the absorbent assembly 60 will have less than about 10% of the stretch of the front and/or back panels, 12 and/or 36 respectively. Most desirably, the absorbent assembly 60 will have less than about 5% of the stretch of the front and/or back panels, 12 and/or 36 respectively.

The reason for making the absorbent assembly 60 non-stretchable is that the front and back panels, 12 and 36 respectively, are elastically stretchable and can expand and contract to snugly conform to the user's anatomy, especially to the wearer's torso. The absorbent assembly 60 is designed not to expand and contract as the front and back panels, 12 and 36 respectively, stretch or retract since the absorbent assembly 60 is bonded to the non-extensible and non-retractable second zones 16 and 40. This feature allows the absorbent assembly 60 to remain positioned over the user's perineum. As the absorbent assembly 60 receives body fluid and/or excrement discharged by the wearer, it will be displaced outward and downward, away from the user's torso. The ability of the absorbent assembly 60 to move outward away from the user's torso as additional body fluid is absorbed and retained is a direct result of the fact that it is not restricted from such movement in the crotch region 82 by the front or back panels, 12 and 36 respectively. The attachments 78 and 80 assure that the absorbent assembly 60 covers the perineum but is capable of moving outward away from the torso as additional body fluid is received and retained.

Referring now to FIGS. 1, 3 and 6, the disposable absorbent article 10 also has at least one elastic member 84 positioned adjacent to and aligned approximately parallel to each of the first and second side edges 74 and 76 of the absorbent assembly 60. Each of the elastic members 84 is situated between the bodyside liner 62 and the outer cover 64. The elastic members 84 provide a gasket to hold the first and second side edges, 74 and 76 respectively, of the absorbent assembly 60 against the user's body. Each of the elastic members 84 can be in the form of an elastic strand, ribbon or strip. Desirably, from two to six elastic members 84 will be positioned adjacent to each of the first and second side edges, 74 and 76 respectively. In FIGS. 3 and 6, two elastic members 84 are shown positioned adjacent to each of the first and second side edges, 74 and 76 respectively. The elastic members 84 are shown as having a round cross-sectional configuration although various other geometrical configurations can be utilized. The elastic members 84 extend parallel to the longitudinal central axis X-X and extend completely through the crotch region 82. Desirably, the ends of the elastic members 84 will be located within the front and back panels, 12 and 36 respectively.

Referring again to FIGS. 1-4, the absorbent assembly 60 is capable of being folded transversely, approximate the transverse central axis Y-Y, to enable the first and second side edges 26 and 28 of the front panel 12 to align with the first and second side edges 50 and 52 of the back panel 36, respectively. A pair of seams 88 and 90 is then formed to join the front panel 12 to the back panel 36. The seam 88 secures the second side edge 28 of the front panel 12 to the second side edge 52 of the back panel 36 while the seam 90 secures the first side edge 26 of the front panel 12 to the first side edge 50 of the back panel 36. One will notice that FIG. 3 is an open view of the interior of the disposable absorbent article 10 and the front panel 12 is folded along the transverse central axis Y-Y such that the front panel 12 lies over the top of the back panel 36. After folding and forming the pair of seams 88 and 90, the disposable absorbent article 10 shown in FIG. 1 is obtained. The disposable absorbent article 10 has a waist opening 92 and a pair of leg openings 94 and 96. Since the front and back panels, 12 and 36 respectively, are formed from a stretchable elastic material, the waist opening 92 and the pair of leg openings 94 and 96 can expand or contract in size to accommodate the anatomy of the user.

Method

Referring now to FIG. 7, a flow diagram is depicted showing a method of manufacturing the disposable absorbent article 10. The method includes the steps of forming a front panel 12 having a first zone 14 and a second zone 16. The first zone 14 is extensible and retractable and the second zone 16 is non-extensible and non-retractable. The front panel 12 also has an inner surface 18, an outer surface 20, a first side edge 26 and a second side edge 28. Furthermore, the second zone 16 is spaced inward from the first and second side edges, 26 and 28 respectively. The method also includes forming a back panel 36 having a first zone 38 and a second zone 40. The first zone 38 is extensible and retractable and the second zone 40 is non-extensible and non-retractable. The back panel 36 also has an inner surface 42, an outer surface 44, a first side edge 50 and a second side edge 52. Furthermore, the second zone 40 of the back panel 36 is spaced inward from the first and second side edges, 50 and 52 respectively, of the back panel 36. The method further includes forming an absorbent assembly 60 having a liquid pervious bodyside liner 62, a liquid-impervious outer cover 64, and an absorbent 66 positioned therebetween. The absorbent assembly 60 has a first end 70 and a second end 72 and the absorbent assembly 60 is secured to the front and back panels, 12 and 36 respectively. The first end 70 of the absorbent assembly 60 is secured to the second zone 16 of the front panel 12 and the second end 72 of the absorbent assembly 60 is secured to the second zone 40 of the back panel 36. The absorbent assembly 60 can be secured to either the inner or outer surfaces 18 and 42 or 20 and 44 of the front and back panels, 12 and 36 respectively. The absorbent assembly 60 is capable of being folded to enable the first and second side edges, 26 and 28 respectively, of the front panel 12 to align with the first and second side edges 50 and 52 respectively, of the back panel 36. Lastly, the method includes joining the front and back panels, 12 and 36 respectively, together by a pair of seams 88 and 90 at the first and second side edges 74 and 76 to form a disposable absorbent article 10 having a waist opening 92 and a pair of leg openings 94 and 96.

While the invention has been described in conjunction with a specific embodiment, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:
1. A disposable absorbent article comprising:
a) a front panel having a first zone and a second zone, said first zone being extensible and retractable and said second zone being non-extensible and non-retractable, said front panel also having a first end, a second end, a first side edge and a second side edge, said first zone extending from said first side edge to said second side edge, and said second zone is spaced inward from said first and second side edges and inward from one of said first end, said second end, or both said first end and said second end, such that said extensible and retractable first zone abuts said first and second side edges along their entire length;
b) a back panel having a first zone and a second zone, said first zone being extensible and retractable and said second zone being non-extensible and non-retractable, said back panel also having a first side edge and a second side edge, and said second zone of said back panel is spaced inward from said first and second side edges of said back panel, wherein said back panel is spaced apart, discontinuous and distinct from said front panel;
c) an absorbent assembly including a liquid pervious bodyside liner, a liquid-impervious outer cover, and an absorbent positioned therebetween, said absorbent assembly having a first end and a second end, said absorbent assembly being secured to said front and back panels, said first end of said absorbent assembly being secured to said second zone of said front panel and said second end of said absorbent assembly being secured to said second zone of said back panel, and said absorbent assembly capable of being folded to enable said first and second side edges of said front panel to align with said first and second side edges of said back panel; and
d) a pair of seams joining said front and back panels together at said first and second side edges to form a disposable absorbent article having a waist opening and a pair of leg openings, said article is designed to be pulled up around a user's torso without having to first open said article.

2. The disposable absorbent article of claim 1 wherein each of said second zones is formed from the same material as said first zone but does not possess extensible and retractable properties.

3. The disposable absorbent article of claim 1 wherein said second zone of said front panel has a smaller surface area than said first zone of said front panel.

4. The disposable absorbent article of claim 3 wherein said second zone of said front panel has a surface area that is less than about 25% of the surface area of said first zone.

5. The disposable absorbent article of claim 4 wherein said second zone of said front panel has a surface area that is less than about 20% of the surface area of said first zone.

6. The disposable absorbent article of claim 1 wherein said front panel has an inner surface and said absorbent assembly is secured to said inner surface, and said front panel has a first end and a second end and said first end of said absorbent assembly is secured at a location that is closer to said second end of said front panel.

7. The disposable absorbent article of claim 1 wherein said back panel has an inner surface and said absorbent assembly is secured to said inner surface, and wherein said second zone of said back panel has a smaller surface area than said first zone of said back panel.

8. The disposable absorbent article of claim 7 wherein said second zone of said back panel has a surface area that is less than about 30% of the surface area of said first zone of said back panel.

9. The disposable absorbent article of claim 1 wherein said second zone of said back panel has a larger surface area than said second zone of said front panel.

10. A disposable absorbent article comprising:
a) a front panel having a first zone and a second zone, said first zone being extensible and retractable and said second zone being non-extensible and non-retractable, said front panel also has a first end, a second end, a first side edge and a second side edge, said first zone extending from said first side edge to said second side edge, and said second zone is spaced inward from said first and second side edges and inward from one of said first end, said second end, or both said first end and said second end, such that said extensible and retractable first zone abuts said first and second side edges along their entire length, such that said extensible and retractable first zone abuts said first and second side edges along their entire length;
b) a back panel having a first zone and a second zone, said first zone being extensible and retractable and said second zone being non-extensible and non-retractable, said back panel also has a first side edge and a second side edge, said second zone of said back panel is spaced inward from said first and second side edges of said back panel, and said second zone of said back panel has a larger surface area than said second zone of said front panel;

c) an absorbent assembly including a liquid pervious bodyside liner, a liquid-impervious outer cover, and an absorbent positioned therebetween, said absorbent assembly having a first end, a second end, a first side edge and a second side edge, said absorbent assembly being secured to said front and back panels, said first end of said absorbent assembly being secured to said second zone of said front panel and said second end of said absorbent assembly being secured to said second zone of said back panel, and said absorbent assembly capable of being folded to enable said first and second side edges of said front panel to align with said first and second side edges of said back panel; and d) at least one elastic member positioned adjacent to each of said first and second side edges of said absorbent assembly and situated between said bodyside liner and said outer cover; and e) a pair of seams joining said first and second side edges of said front and back panels together to form a disposable absorbent article having a waist opening and a pair of leg openings, said article is designed to be pulled up around a user's torso without having to first open said article.

11. The disposable absorbent article of claim 10 wherein said back panel has an inner surface and said absorbent assembly is secured to said inner surface, and said second zone of said back panel has a larger surface area than said second zone of said front panel.

12. The disposable absorbent article of claim 10 wherein said front panel has an inner surface and said absorbent assembly is secured to said inner surface, and said front panel has a first end and a second end and said first end of said absorbent assembly is secured at a location that is closer to said second end of said front panel.

13. The disposable absorbent article of claim 10 wherein said back panel has a first end and a second end and said second end of said absorbent assembly is secured at a location that is closer to said second end of said back panel.

14. The disposable absorbent article of claim 10 wherein said second zone of said front panel is rectangular in configuration.

15. The disposable absorbent article of claim 10 wherein said second zone of said back panel is rectangular in configuration.

16. A method of forming a disposable absorbent article comprising the steps of:

a) forming a front panel having a first zone and a second zone, said first zone being extensible and retractable and said second zone being non-extensible and non-retractable, said front panel also having a first end, a second end, first side edge and a second side edge, said first zone extending from said first side edge to said second side edge, and said second zone is spaced inward from said first and second side edges and inward from one of said first end, said second end, or both said first end and said second end, such that said extensible and retractable first zone abuts said first and second side edges along their entire length;

b) forming a back panel having a first zone and a second zone, said first zone being extensible and retractable and said second zone being non-extensible and non-retractable, said back panel also having a first side edge and a second side edge, and said second zone of said back panel is spaced inward from said first and second side edges of said back panel;

c) forming an absorbent assembly having a liquid pervious bodyside liner, a liquid-impervious outer cover, and an absorbent positioned therebetween, said absorbent assembly having a first end and a second end;

d) securing said absorbent assembly to said front and back panels, said first end of said absorbent assembly being secured to said second zone of said front panel and said second end of said absorbent assembly being secured to said second zone of said back panel;

e) folding said absorbent assembly so that said first and second side edges of said front panel are aligned with said first and second side edges of said back panel; and f) joining said front and back panels together by a pair of seams formed at said first and second side edges to form a disposable absorbent article having a waist opening and a pair of leg openings, said article is designed to be pulled up around a user's torso without having to first open said article.

17. The method of claim 16 wherein each of said front and back panels has an inner surface and said absorbent assembly is secured to said inner surfaces of said front and back panels.

18. The method of claim 16 wherein each of said front and back panels has an outer surface and said absorbent assembly is secured to said outer surfaces of said front and back panels.

19. The method of claim 16 wherein said first zone of said front and back panels encloses three sides of said second zone.

20. The method of claim 16 wherein said second zone of said front and back panels is not extended before said absorbent assembly is secured thereto.

* * * * *